United States Patent [19]

Lönnstedt

[11] Patent Number: 4,615,050
[45] Date of Patent: Oct. 7, 1986

[54] HEADBAND STRUCTURE FOR EAR COVERINGS

[76] Inventor: Bo G. Lönnstedt, Kvarnbergsvägen 23, S-14145 Huddinge, Sweden

[21] Appl. No.: 751,225

[22] Filed: Jul. 2, 1985

[30] Foreign Application Priority Data

Jul. 4, 1984 [SE] Sweden ............................... 8403547

[51] Int. Cl.⁴ ................... A42B 1/06; H04R 1/10; H04M 1/05
[52] U.S. Cl. ............................ 2/209; 179/156 R; 181/129; 267/181
[58] Field of Search ............. 248/626; 2/209; 24/545; 267/47, 160, 181, 164; 16/225; 181/129; 179/156 R, 156 A, 182 R, 182 A, 184; 381/25

[56] References Cited

U.S. PATENT DOCUMENTS

| | | | |
|---|---|---|---|
| 3,057,028 | 10/1962 | Lorber | 24/545 |
| 3,682,268 | 8/1972 | Gorike | 179/156 R X |
| 3,754,300 | 8/1973 | Shepherd | 16/225 |
| 3,793,612 | 2/1974 | Driscoll | 16/225 X |
| 4,065,645 | 12/1977 | Warner et al. | 179/156 R |
| 4,192,441 | 3/1980 | Batts | 24/545 X |
| 4,551,584 | 11/1985 | Mathiasen | 179/156 R |

FOREIGN PATENT DOCUMENTS

| | | | |
|---|---|---|---|
| 2132817 | 1/1972 | Fed. Rep. of Germany | 179/156 R |
| 57-179444 | 11/1982 | Japan | 267/164 |

*Primary Examiner*—Werner H. Schroeder
*Assistant Examiner*—Andrew M. Falik
*Attorney, Agent, or Firm*—Young & Thompson

[57] ABSTRACT

A stirrup-shaped support for supporting ear protectors for example has two end parts, between which there is located an intermediate part incorporating an inner section and an outer section. When the end parts are moved away from one another, the inner section is arranged to be subjected to a tensile force while the outer section is arranged to buckle, at the same time, towards the inner section. The rigidity of the outer section is such that the force required to move the end parts away from each other is substantially constant within a predetermined range of distances between the end parts.

7 Claims, 8 Drawing Figures

HEADBAND STRUCTURE FOR EAR COVERINGS

The present invention relates to a stirrup-shaped support having two end parts which are connected through an intermediate part and which are intended to headband structure for ear coverings, and more particularly to support members, such as ear protectors, intended to be placed against the ears of a wearer.

The need of being able to support, for example, ear pads for protecting the hearing of a wearer, with the aid of a stirrup-shaped support, prevails in many different contexts. Since different people have different sized heads, i.e. mutually different distances between the openings of the auditory meatus, the distance between the ends of the support will vary with different people. One disadvantage inherent with present day stirrup-shaped supports is that the force required to move the support ends away from each other varies with the distance between the ends. As a result hereof, the contact force will vary with the head size, wherewith the noise-attenuating properties of, for example, an ear-muff intended to protect the hearing of a wearer, will vary from person to person.

The object of the invention is to provide an improved stirrup-like support structure which is not encumbered with the earlier disadvantages and with which the force of contact is substantially the same for all wearers, irrespective of head size.

This object is achieved by means of the invention in that the intermediate support part incorporates in at least one location thereon an inner elongated section which is intended to lie close to the head of the wearer, and an outer elongated section lying externally of the inner section; in that when moving the two end parts of the support away from each other in the in-use position, the inner section is arranged to be subjected to a tensile force while the outer section is arranged to buckle in towards the inner section; and in that the buckling resistance of the outer section is so adapted that the force required to move the support end parts away from each other is substantially constant within a predetermined range of distances between the end parts.

It is ensured with a stirrup-shaped support of this design that when used in conjunction with different types of ear protector pads, the contact force will be the same for all wearers, irrespective of head size.

The invention will now be described in more detail with the aid of exemplary embodiments thereof illustrated in the accompanying drawings, in which.

Figure 1:
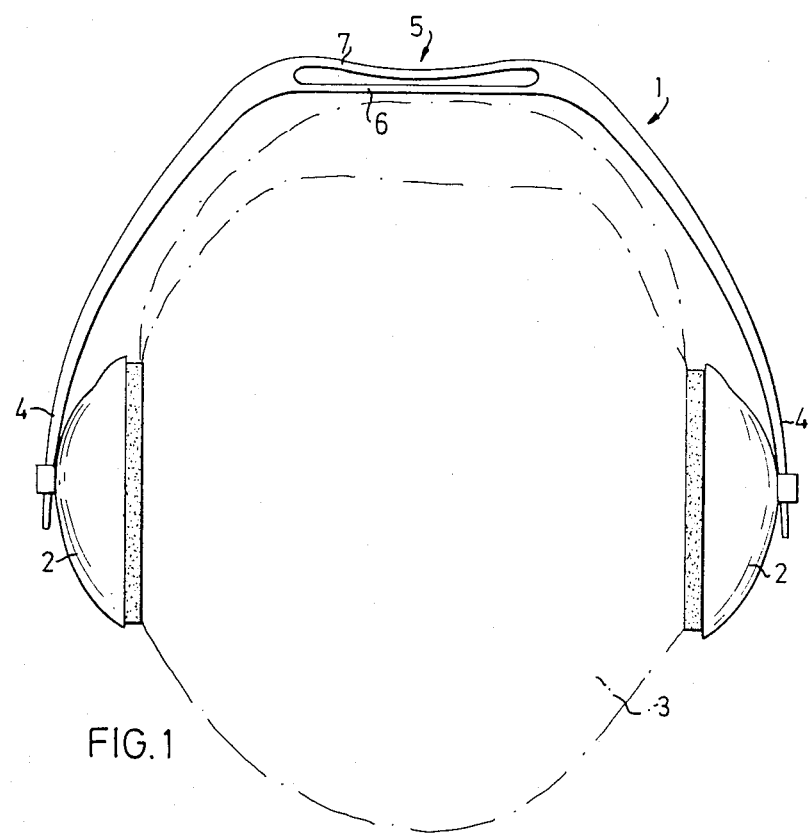
FIG. 1 illustrates a stirrup-shaped support according to the invention with the support in its in-use position.

A stirrup-shaped support 1 illustrated in FIG. 1 and constructed in accordance with the invention is provided with ear protectors 2 and is shown fitted to the head 3 of a wearer. The stirrup-shaped support 1 has two end parts 4 which are interconnected through an intermediate part 5 which incorporates an inner section 6 and an outer section 7. In the in-use position of the support, the outer section 7 is curved arcuately down towards the inner section 6, this inner section being subjected to a tensile force at the same time.

Figure 2:
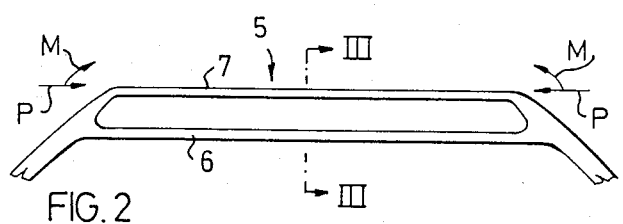
FIG. 2 illustrates a detail of the support shown in FIG. 1, in a relaxed state.
Figure 3:
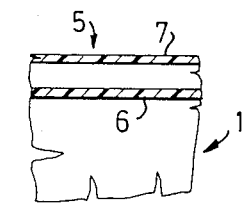
FIG. 3 is a sectional view taken on the line III—III in FIG. 2.

FIGS. 2 and 3 illustrate the intermediate part 5 in a relaxed state, and it will be seen herefrom that in the relaxed state of the part 5, the inner section 6 and the outer section 7 are substantially straight and parallel with one another. The sections of the illustrated embodiment are substantially of equal length, thickness and width, although the sections may, of course, be dimensioned differently, depending on the material from which they are made. It will be seen that as the end parts of the support are moved away from one another, the two ends of the outer section 7 will be subjected to a pressure load P and a bending moment M, in accordance with the arrows shown in FIG. 2. When the pressure force P and the bending moment M reach a given magnitude, the outer section 7 will buckle in towards the inner section 6, thereby reducing the vertical distance between the opposing surfaces of the inner and outer sections as illustrated in FIG. 1.

Figure 8:
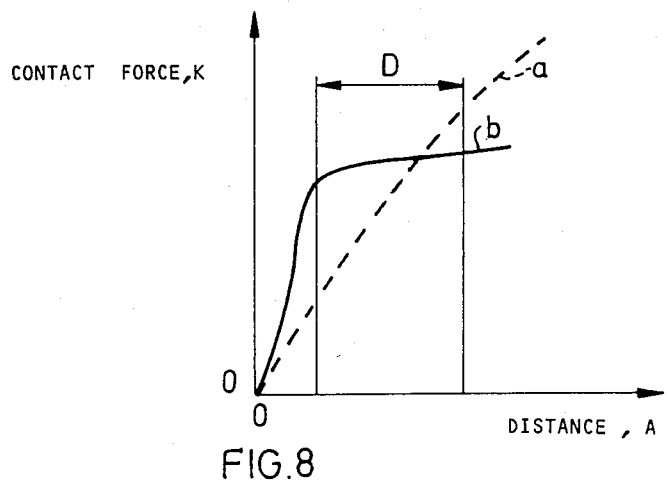
FIG. 8 is a diagram illustrating the relationship between the contact force and the distance from a rest position of the arm of a stirrup-shaped support according to the invention.

When using a stirrup-shaped support provided with ear protectors, each end part 4 is swung out from a rest position through a requisite distance. In known types of supports, the contact force increases with the extent to which the protectors are swung out from their rest position, as illustrated by the curve a in FIG. 8, where the contact force K is shown diagrammatically as a function of the distance A from the rest position. In the case of a stirrup-shaped support according to the invention, the contact force will vary in a completely different manner, namely in accordance with the curve b. As illustrated in FIG. 8, the curve b transforms into a substantially horizontal line when a certain level is reached, indicating that at this level the contact force K remains substantially constant for different values of the distance A. The distance D in FIG. 8 illustrates a typical interval within which an end part 4 is required to move in order to accommodate different head sizes.

It has been determined empirically that the width of the heads of different people, measured between the auditory meatus openings, varies from between about 130 mm and about 170 mm. Consequently, the two end parts of a stirrup-shaped support must cover an interval of about 40 mm in order to enable the support to be used by different people. This involves a change in distance of about 20 mm for each end part. However, in order to be on the safe side, the distance D should be greater than 20 mm, suitably in the order of about 30 to 40 mm. The stirrup-shaped support according to the invention thus provides a contact force which varies to only an insignificant extent with increasing distances between the two end parts of the support, thereby enabling the contact force to be varied to an optimum with respect, for example, to the dampening of sound and noise when used in conjunction with ear protectors.

Figure 4:
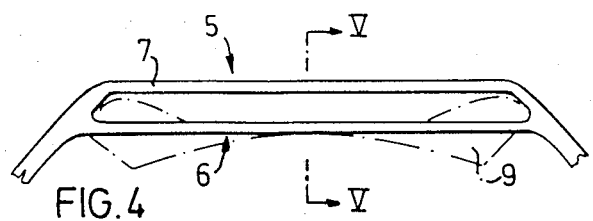
FIG. 4 illustrates a detail corresponding to that shown in FIG. 2 of a further embodiment of the stirrup-shaped support shown in FIG. 1.
Figure 5:
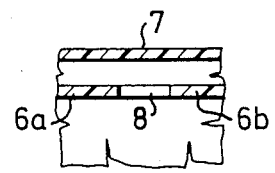
FIG. 5 is a sectional view taken on the line V—V in FIG. 4.

In an alternative embodiment illustrated in FIGS. 4 and 5, the inner section 6 is provided with an opening 8 through which, for example, a head rest 9 can be fitted to the stirrup-shaped support 1. The opening 8 may advantageously extend along the whole of the inner section 6, so as to divide said section into side members 6a and 6b, as shown in FIG. 5.

Figure 6:
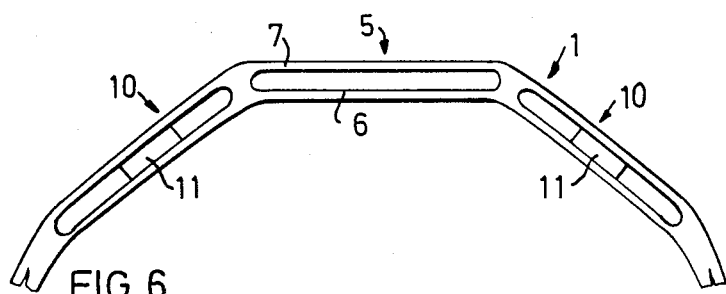
FIGS. 6 and 7 illustrate part of further variants of the stirrup-shaped support according to the invention.

As illustrated in FIG. 6, there may be provided on a respective side of the intermediate part 5 at least one outwardly lying part 10 corresponding to the intermediate part 5. These outwardly lying parts 10 may be shorter or longer than the intermediate part 5, but should be more rigid than said intermediate part, so that the intermediate part buckles before either of the two outwardly lying parts 10. This can be achieved, for example, by introducing into the outwardly lying parts 10 some form of soft spacing means 11, to provide the desired degree of inflexibility. The spacer may comprise a piece of foamed plastics or like material for example. Naturally it is also possible to produce the degree of rigidity desired in each of the outwardly lying parts 10 by suitable dimensioning of the actual body structure of the support.

Figure 7:
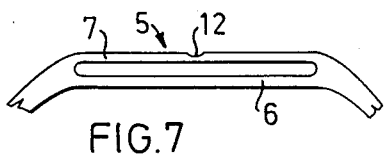

In certain cases it may be desirable to ensure that the outer section 7 will buckle symmetrically. To this end, a suitably formed notch or score-line 12 may be provided centrally of the outer section 7, suitably in the side thereof remote from the inner section 6, as shown in FIG. 7.

The stirrup-shaped support according to the invention may be moulded from a plastics material, although other materials may be used of course. It will also be understood that although the outer section 7 of the illustrated embodiments is straight, the section may instead be curved, and then suitably with an initial curvature in a direction towards the inner section 6. Furthermore, the outer section 7 can be divided into mutually adjacent parts, in a manner similar to that shown for the inner section in FIG. 5.

I claim:

1. A stirrup-shaped support for ear protectors, having two end parts which are joined through a central intermediate part, the intermediate part having in at least one location thereon an inner elongated section which is intended to lie close to the head of the wearer, and an outer elongated section lying externally of and spaced from the inner section; the inner and outer sections being so configured that when moving the two end parts of the support away from each other in the in-use position, the inner section is subjected to a tensile force at the same time as the outer section buckles in toward the inner section whereby the vertical distance between the opposing surfaces of the said inner and outer sections is decreased; the buckling resistance of the outer section being such that the force required to move the support end parts away from one another is substantially constant within a predetermined range of distances between the end parts.

2. A support according to claim 1, in which the inner and the outer sections are substantially straight and mutually parallel when in their relaxed state.

3. A support according to claim 1, in which the inner section has an opening for the mounting of a head rest.

4. A support according to claim 3, in which the opening extends along the whole of the inner section, thereby to divide the section into two side members.

5. A support according to claim 1, in which located on each side of the intermediate part is at least one outwardly lying part formed in a manner corresponding to the intermediate part; the rigidity of said outwardly lying part being greater than that of the intermediate part.

6. A support according to claim 1, in which the outer section has a notch located centrally thereon, to facilitate buckling of said outer section.

7. A support according to claim 1, made of a plastic material.

* * * * *